United States Patent
Bruna et al.

(10) Patent No.: US 9,365,341 B2
(45) Date of Patent: Jun. 14, 2016

(54) DISTRIBUTION DEVICE AND PRODUCTION METHOD THEREOF

(75) Inventors: Pascal Bruna, Rouen (FR); Florent Dauguet, Jouy sur Eure (FR); Jérôme Langeard, Bois Guillaume (FR); Nicolas Oblin, La Saussaye (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 14/125,742

(22) PCT Filed: Jun. 11, 2012

(86) PCT No.: PCT/FR2012/051302
§ 371 (c)(1),
(2), (4) Date: Dec. 12, 2013

(87) PCT Pub. No.: WO2012/172243
PCT Pub. Date: Dec. 20, 2012

(65) Prior Publication Data
US 2014/0103064 A1    Apr. 17, 2014

(30) Foreign Application Priority Data
Jun. 14, 2011 (FR) ..................... 11 55154

(51) Int. Cl.
*B67D 7/06* (2010.01)
*B65D 83/00* (2006.01)
(Continued)

(52) U.S. Cl.
CPC ........... *B65D 83/00* (2013.01); *A61M 15/0051* (2014.02); *A61M 15/0068* (2014.02); *B65D 75/327* (2013.01); *A61M 2202/064* (2013.01); *A61M 2205/3306* (2013.01); *A61M 2205/60* (2013.01); *A61M 2205/6063* (2013.01); *A61M 2205/6072* (2013.01); *B65D 2203/00* (2013.01); *B65D 2203/06* (2013.01)

(58) Field of Classification Search
USPC ........................... 222/23, 321.1, 321.6–321.9
See application file for complete search history.

(56) References Cited

U.S. PATENT DOCUMENTS

| | | | |
|---|---|---|---|
| 5,192,006 A * | 3/1993 | Van Brocklin et al. | 222/321.9 |
| 5,507,411 A * | 4/1996 | Peckels | 222/1 |
| 7,690,533 B2 * | 4/2010 | Stilley | 222/113 |

(Continued)

FOREIGN PATENT DOCUMENTS

| FR | 2864035 A1 * | 6/2005 |
|---|---|---|
| FR | 2 911 421 A1 | 7/2008 |

(Continued)

OTHER PUBLICATIONS

English translation of the International Preliminary Report on Patentability for PCT/FR2012/051302.

(Continued)

*Primary Examiner* — Donnell Long
(74) *Attorney, Agent, or Firm* — Sughrue Mion, PLLC

(57) ABSTRACT

A fluid dispenser device having at least one reservoir containing fluid to be dispensed and dispenser mechanism that is actuatable by a user so as to dispense the fluid through a dispenser orifice. The dispenser device having a plurality of assembled-together component parts, at least one of the component parts including a unique marking so that each individual dispenser device is identifiable and/or traceable by the unique marking.

20 Claims, 2 Drawing Sheets

(51) Int. Cl.
*B65D 75/32* (2006.01)
*A61M 15/00* (2006.01)

(56) References Cited

U.S. PATENT DOCUMENTS

| | | | |
|---|---|---|---|
| 8,091,735 B2 * | 1/2012 | Girard et al. | 222/54 |
| 2001/0004083 A1 * | 6/2001 | Brotspies et al. | 222/162 |
| 2004/0124213 A1 * | 7/2004 | Gillissen et al. | 222/321.6 |
| 2004/0144805 A1 * | 7/2004 | Maner | 222/321.6 |
| 2005/0022806 A1 * | 2/2005 | Beaumont et al. | 128/200.14 |
| 2005/0070841 A1 * | 3/2005 | Mathiesen et al. | 604/20 |
| 2005/0274378 A1 * | 12/2005 | Bonney et al. | 128/200.23 |
| 2007/0179448 A1 * | 8/2007 | Lim et al. | 604/187 |
| 2008/0121050 A1 * | 5/2008 | Sakal et al. | 73/863.21 |
| 2008/0290168 A1 * | 11/2008 | Sullivan et al. | 235/462.01 |
| 2011/0166699 A1 * | 7/2011 | Palmquist | 700/236 |

FOREIGN PATENT DOCUMENTS

| | | |
|---|---|---|
| WO | 02/095675 A1 | 11/2002 |
| WO | WO 2011054402 A1 * | 5/2011 |

OTHER PUBLICATIONS

International Search Report for PCT/FR2012/051302 dated Oct. 19, 2012.

* cited by examiner

DISTRIBUTION DEVICE AND PRODUCTION METHOD THEREOF

CROSS REFERENCE TO RELATED APPLICATIONS

This application is a National Stage of International Application No. PCT/FR 2012/051302 filed Jun. 11, 2012, claiming priority based on French Patent Application No. 11 55154 filed Jun. 14, 2011, the contents of all of which are incorporated herein by reference in their entirety.

The present invention relates to a fluid dispenser device and to a method of manufacturing such a device.

Nowadays, there is an ever increasing requirement in the industrial world for traceability of products that are manufactured and sold. This requirement is particularly important in the pharmaceutical field, and in particular for dispenser devices for dispensing pharmaceuticals. Such traceability serves in particular to make it easier to identify causes in the event of the device malfunctioning, and also to guarantee the origin of devices compared to counterfeit devices. Currently, in the field of fluid dispenser devices of the pharmaceutical type, that are sometimes manufactured at rates and in quantities that are very high, typically several million units per year, only batches, which may contain several tens of thousands of devices, are identifiable once the devices have been put on the market. Thus, it may be very difficult to understand why a particular device has suffered a malfunction. It is generally possible to locate the batch to which it belongs and thus the general conditions and the date on which the batch was manufactured, but, within said batch, it is impossible to determine which devices have suffered the malfunction and why. Another problem that generally occurs with fluid dispenser devices of the pharmaceutical type, in particular when they are not very complex, relates to the way in which the user must use the device in order to guarantee that it operates properly. The operating instructions are generally included in the box that contains the device, but the operating instructions might be thrown away or lost by the user, who then has no easy means of finding out the correct way to use the device. In addition, the side effects of the pharmaceutical and its dosage may also pose certain problems when the operating instructions are no longer available. In the prior art, it has been proposed to provide an electronic chip, such as a radio-frequency identification (RFID) tag, on various portions of a fluid dispenser device. That is costly and requires the use of electronic elements on the device that might malfunction. Document WO 02/095675 describes such an arrangement.

An object of the present invention is to overcome the above-mentioned drawbacks.

In particular, an object of the present invention is to provide a fluid dispenser device and its method of manufacture that guarantee that each individual dispenser device can be traced and/or identified regardless of the number of devices that have been manufactured.

Another object of the present invention is to provide such a fluid dispenser device and its method of manufacture that make it possible to improve communication with the user of the device.

Another object of the present invention is to provide a fluid dispenser device and its method of manufacture that are simple and inexpensive to make or to perform.

The present invention thus provides a fluid dispenser device comprising at least one reservoir containing fluid to be dispensed and dispenser means that are actuatable by a user so as to dispense the fluid through a dispenser orifice, said dispenser device comprising a plurality of assembled-together component parts, at least one of said component parts including a unique marking so that each individual dispenser device is identifiable and/or traceable by means of said unique marking, said unique marking being a bar code or a 2D or 3D matrix code.

Advantageously, said unique marking is an individual identification code that associates each individual dispenser device with an individual computer file containing technical information relating to said individual dispenser device.

Advantageously, said technical information includes information relating to the methods of manufacturing, assembling, and/or filling said dispenser device, such as the molding, assembling, and control parameters.

Advantageously, said unique marking is applied to said at least one component part by silk-screen printing, marking by ultraviolet rays, hot marking, stamping, punching, electrochemical marking, marking by micro-percussion, marking by ink jet, pad printing, and/or laser marking.

Advantageously, said laser marking is performed by $CO_2$ laser, fiber laser, or diode laser.

Advantageously, said at least one component part is made of rigid plastics material, of flexible plastics material, of metal, of glass, or of ceramic.

Advantageously, said unique marking is formed on a label that is fastened to said at least one component part.

Advantageously, said matrix code contains readable information that can be read by means of a matrix-code reader.

Advantageously, said readable information includes technical information relating to said individual dispenser device, so as to guarantee that each individual dispenser device can be traced.

Advantageously, said readable information contains information relating to the use of said individual dispenser device and/or relating to said fluid to be dispensed, for the purpose of informing a user.

Advantageously, said fluid is a pharmaceutical fluid.

Advantageously, said at least one component part is: a pump or valve body; a crimping cap for fastening such a body on a reservoir; a pusher for actuating a pump or a valve, in particular a nasal pusher; a glass reservoir, such as a syringe or a carpule; a reservoir made of plastics material; a group of individual reservoirs, such as a blister strip for an inhaler; a portion of an inhaler, such as the body or the cover of said inhaler; a single-dose or dual-dose device; a dose counter.

Advantageously, said unique marking occupies an area of less than 25 square millimeters ($mm^2$), advantageously less than 16 $mm^2$, preferably less than 9 $mm^2$.

The present invention also provides a method of manufacturing a fluid dispenser device comprising at least one reservoir containing fluid to be dispensed and dispenser means that are actuatable by a user so as to dispense the fluid through a dispenser orifice, said dispenser device comprising a plurality of assembled-together component parts, said method comprising making a unique marking on at least one of said component parts, so as to make each individual dispenser device identifiable and/or traceable.

Advantageously, said step of making the unique marking lasts less than one second, advantageously less than half a second for each marking.

These characteristics and advantages and others of the present invention appear more clearly from the following detailed description, given by way of non-limiting example, and with reference to the accompanying drawings, and in which FIG. 1 is a diagrammatic side view of a powder inhaler to which the present invention can be applied;

As can be understood from the description below, the present invention applies more particularly to fluid dispenser devices in the pharmaceutical field, but naturally it could also apply to other technical fields, such as perfumery, and cosmetics, for example.

Figure 1:
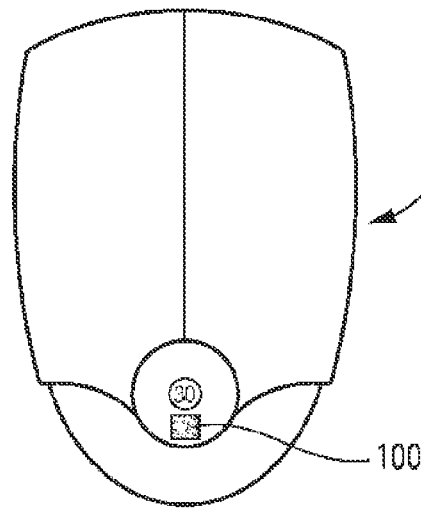
Figure 2:
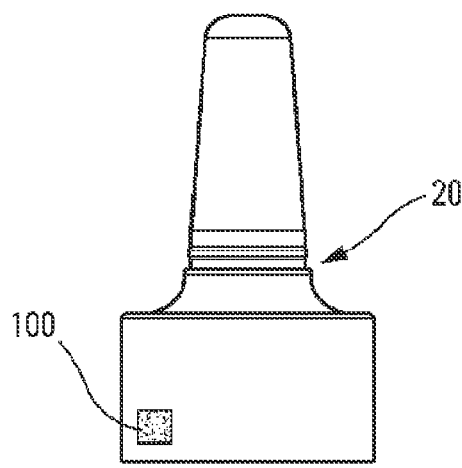
FIG. 2 is a diagrammatic view of a nasal pusher incorporating the present invention.
Figure 3:
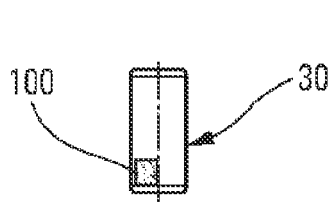
FIG. 3 shows a carpule, typically used in single-dose or dual-dose devices.
Figure 4:
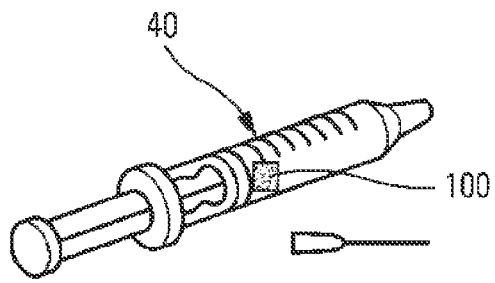
FIG. 4 shows a syringe.
Figure 5:
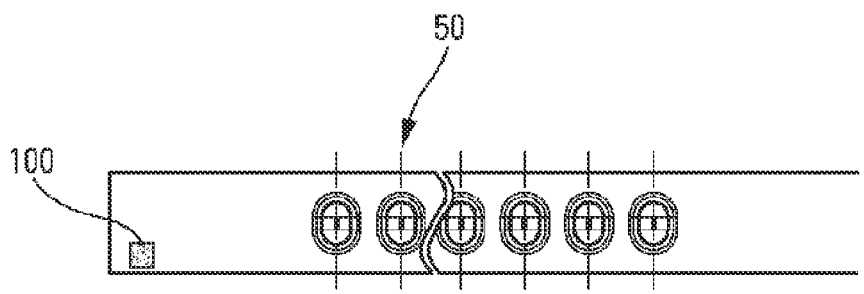
FIG. 5 is a blister strip for an inhaler, in particular a powder inhaler.
Figure 6:
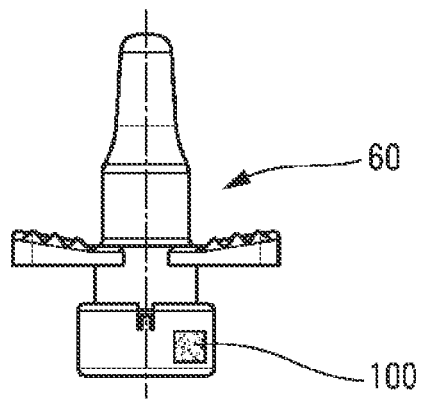
FIG. 6 is a single-dose or dual-dose type device.
Figure 7:
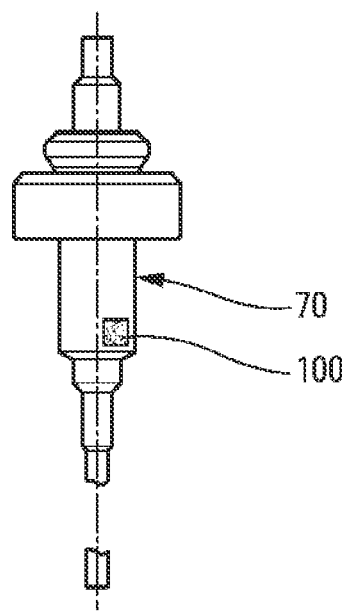
FIG. 7 is a pump body.
Figure 8:
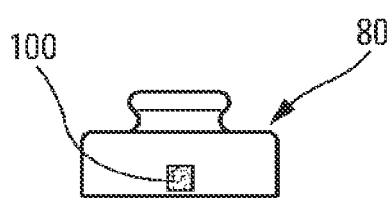
FIG. 8 is a crimping capsule for a pump or valve.

The present invention makes provision for a unique marking 100 on each individual fluid dispenser device, which marking makes the individual device identifiable and/or traceable. The various figures show various component parts for various types of fluid dispenser device to which a unique marking may be applied. Thus, it should be observed that the unique markings may be applied to surfaces that are external and thus visible to the user, or internal and thus not visible to the user. The advantages of the two variants are described below. In addition, the unique marking 100 may be applied to a plane surface, but it may also be applied to a curved surface, as shown in FIGS. 2, 3, 4, 6, 7, and 8, for example. Naturally, other devices or other component parts of fluid dispenser devices may be subjected to marking, and the examples shown in the drawings are non-limiting. Thus, by way of example, counter devices such as dose counters could also be marked in accordance with the present invention.

Depending on the complexity of the fluid dispenser device, a plurality of markings could be applied to various component parts of a single fluid dispenser device, in particular when a final assembly step is performed by the manufacturer of the fluid to be dispensed.

The component part that receives the marking may thus be made of various materials, e.g. flexible or rigid plastics materials, glass, metal, or ceramics.

Advantageously, an individual computer file is associated with each unique marking, which computer file contains technical information relating to said individual marked dispenser device. By way of example, the technical information may include elements relating to the methods of manufacturing, assembling, and filling the device, and in particular the molding, assembling, and control parameters of said device. Thus, by means of the marking, it is always possible to find such information for each individual device, thereby guaranteeing absolute traceability. Pertinent technical information includes the type of machine used, the speed of the machine, and thus its production rate, the speed of its cylinder, the identity of the machine operator, and any digital information associated with the key sensors that are managed by automatic machines and stored in production data files. Naturally, other information is also potentially storable.

Various ways of making said markings can be envisaged. Thus, it is possible to use silk-screen printing, in particular a print from a taut canvas that may be made of silk or of polyamide. This implementation presents the advantages of enabling strong colors to be used and of being compatible with any type of medium, such as paper, cardboard, wood, plastics, rubber, various metals, glass, and textile in particular. In a variant, it is also possible to use ultraviolet digital marking that enables marking to be of very high precision and that is compatible with the majority of media that accept ultraviolet rays for drying the inks. Hot marking is also envisaged since it makes very high throughput rates possible, possibly achieving up to ten thousand pieces per hour with embossing systems. Cold marking, i.e. by stamping or punching, is also possible, and it is compatible with any type of medium providing it is possible to exceed the elastic limit of the material under consideration. Electrochemical marking can be used for marking on hard or soft materials. Micropercussion marking makes it possible to produce markings on steel, plastics, glass, etc. Marking by ink jet also makes it possible to mark any type of material, as does pad printing.

Particularly advantageous marking, and probably one of the most suitable for the present invention is, however, laser marking. Various technologies may be used, e.g. $CO_2$ lasers, fiber lasers, or diode lasers. Other types of laser can also be envisaged. Laser marking is compatible with any material, and this is particularly advantageous in the field of pharmacy in which materials of a wide variety of different types are used.

Advantageously, the marking may be of very small size, typically of a few $mm^2$. Thus, it may be desired for the marking to have an area less than 25 $mm^2$, advantageously even less than 16 $mm^2$, preferably less than 9 $mm^2$. Even smaller markings are possible depending on the technology used to make the markings.

Advantageously, marking rates must be compatible with industrial manufacturing methods. Typically, the time taken to make one marking should be less than 1 second (s), and preferably less than 0.5 s, so as to enable throughput rates of 120 to 150 pieces per minute.

For marking on a curved surface, it may be desirable to distort the marking deliberately so as to compensate for the curvature during reading. This technique is particularly desirable if the marking is for reading by a future user by means of an appropriate reader device.

Various types of marking may be envisaged.

A variant embodiment consists in marking bar codes that are well known in the food industry in order to guarantee that products can be traced.

A particularly advantageous embodiment of the present invention relates to matrix codes, typically two-dimensional or three-dimensional matrix codes, that are referred to as 2D or 3D matrix codes, and that make it possible not only to formally identify a marked device, but also to contain information that is potentially readable by a user provided with an appropriate reader device.

This variant embodiment is shown in the figures. The marking 100 is thus a small square that is constituted by black and white dots that define a code. Examples of this type of 2D matrix code are the codes referred to as Datamatrix and QR codes. With an appropriate reader, generally available on mobile phones, a user can thus access the information contained in said marking. The information may be either technical information, such as information relating to manufacturing or device parameters, for the purpose of traceability, or information for the user of the device, such as the operating instructions or how to use or clean the device, for example. The information on the fluid to be dispensed may also be incorporated in the code. In this event, the marking must naturally be provided on a surface that is visible to the user, so that the user can easily read the information contained therein with a reader.

Thus, the present invention provides numerous advantages for users of fluid dispenser devices, in particular in the field of pharmacy. Thus, by way of example, when there is a malfunctioning problem, such as a poorly assembled or blocked nasal pusher 20, it is possible to know exactly what the characteristics of the particular pusher were, as measured while it was being assembled. It is thus possible to know whether it lies well within the specification or whether it is atypical compared to the rest of the population of the batch to which it belonged. Equivalent applications are obviously possible for any type of device such as pumps or valves, inhalers, syringes, single-dose devices, etc.

Anti-counterfeiting verification codes are also desirable for maximum security and, as explained above, provision may be made for the patient to use a mobile phone to consult the operating instructions or the instructions on how to clean the device if necessary.

Although the present invention is described above with reference to various variant embodiments, naturally it is not limited to those variants, but, on the contrary, any useful modifications could be applied thereto by a person skilled in the art, without going beyond the ambit of the present invention, as defined by the accompanying claims.

The invention claimed is:

1. A fluid dispenser device comprising at least one reservoir containing fluid to be dispensed and dispenser means that are actuatable by a user so as to dispense the fluid through a dispenser orifice, said dispenser device comprising a plurality of assembled-together component parts, wherein at least one of said component parts includes a unique marking so that each individual dispenser device is identifiable and/or traceable by said unique marking, said unique marking being a bar code or a 2D or 3D matrix code; and wherein the fluid dispenser device is free of electronic elements; and wherein said unique marking is an individual identification code that associates each individual dispenser device with an individual computer file containing technical information relating to said individual dispenser device.

2. The device according to claim 1, wherein said technical information includes information relating to the methods of manufacturing, assembling, and/or filling said dispenser device.

3. The device according to claim 1, wherein said unique marking is applied to said at least one component part by silk-screen printing, marking by ultraviolet rays, hot marking, stamping, punching, electrochemical marking, marking by micro-percussion, marking by ink jet, pad printing, and/or laser marking.

4. The device according to claim 3, wherein said unique marking is applied by laser marking is performed by $CO_2$ laser, fiber laser, or diode laser.

5. The device according to claim 1, wherein said at least one component part is made of rigid plastics material, of flexible plastics material, of metal, of glass, or of ceramic.

6. The device according to claim 1, wherein said unique marking is formed on a label that is fastened to said at least one component part.

7. The device according to claim 1, wherein said fluid is a pharmaceutical fluid.

8. The device according to claim 1, wherein said unique marking occupies an area of less than 25 $mm^2$.

9. The device according to claim 1, wherein said technical information includes information relating to the methods of manufacturing, assembling, and/or filling said dispenser device, including at least one of molding, assembling, or control parameters.

10. The device according to claim 1, wherein said technical information includes information relating to the methods of manufacturing, assembling, and/or filling said dispenser device, including molding, assembling, and control parameters.

11. The device according to claim 1, wherein said unique marking occupies an area of less 16 $mm^2$.

12. The device according to claim 1, wherein said unique marking occupies an area of less than 9 $mm^2$.

13. A fluid dispenser device comprising at least one reservoir containing fluid to be dispensed and dispenser means that are actuatable by a user so as to dispense the fluid through a dispenser orifice, said dispenser device comprising a plurality of assembled-together component parts, wherein at least one of said component parts includes a unique marking so that each individual dispenser device is identifiable and/or traceable by said unique marking, said unique marking being a 2D or 3D matrix code; and wherein the fluid dispenser device is free of electronic elements; and wherein said matrix code contains readable information that can be read by a matrix-code reader, said readable information includes technical information relating to said individual dispenser device, so as to guarantee that each individual dispenser device can be traced.

14. The device according to claim 13, wherein said unique marking is an individual identification code that associates each individual dispenser device with an individual computer file containing technical information relating to said individual dispenser device.

15. The device according to claim 13, wherein said technical information includes information relating to at least one of methods of manufacturing, assembling, or filling said dispenser device.

16. A fluid dispenser device comprising at least one reservoir containing fluid to be dispensed and dispenser means that are actuatable by a user so as to dispense the fluid through a dispenser orifice, said dispenser device comprising a plurality of assembled-together component parts, wherein at least one of said component parts includes a unique marking so that each individual dispenser device is identifiable and/or traceable by said unique marking, said unique marking being a 2D or 3D matrix code; and wherein the fluid dispenser device is free of electronic elements;

wherein said matrix code contains readable information that can be read by a matrix-code reader; and wherein said readable information contains information relating to the use of said individual dispenser device and/or relating to said fluid to be dispensed, for the purpose of informing a user.

17. The device according to claim 16, wherein said readable information includes technical information relating to said individual dispenser device, so as to guarantee that each individual dispenser device can be traced.

18. A fluid dispenser device comprising at least one reservoir containing fluid to be dispensed and dispenser means that are actuatable by a user so as to dispense the fluid through a dispenser orifice, said dispenser device comprising a plurality of assembled-together component parts, wherein at least one of said component parts includes a unique marking so that each individual dispenser device is identifiable and/or traceable by said unique marking, said unique marking being a bar code or a 2D or 3D matrix code; and wherein the fluid dispenser device is free of electronic elements;

wherein said at least one component part is: a pump or valve body; a crimping cap for fastening such a body on a reservoir; a pusher for actuating a pump or a valve; a glass reservoir; a reservoir made of plastics material; a group of individual reservoirs; a portion of an inhaler; a single-dose or dual-dose device; a dose counter; wherein the glass reservoir is a syringe body or a carpule.

19. A method of manufacturing a fluid dispenser device comprising at least one reservoir containing fluid to be dispensed and dispenser means that are actuatable by a user so as to dispense the fluid through a dispenser orifice, said dispenser device comprising a plurality of assembled-together component parts, wherein the method comprises making a unique marking on at least one of said component parts, so as to make each individual dispenser device identifiable and/or traceable; and wherein the fluid dispenser device is free of electronic elements and wherein said unique marking is an individual identification code that associates each individual dispenser device with an individual computer file containing technical information relating to said individual dispenser device.

20. The method according to claim 19, in which said step of making the unique marking lasts less than one second for each marking.

\* \* \* \* \*